(12) United States Patent
Matsui

(10) Patent No.: US 11,111,187 B2
(45) Date of Patent: Sep. 7, 2021

(54) PRODUCTION METHOD FOR FULVIC ACID SOLUTION, AND FULVIC ACID SOLUTION

(71) Applicant: G-8 INTERNATIONAL TRADING CO., LTD., Hiratsuka (JP)

(72) Inventor: Saburo Matsui, Hiratsuka (JP)

(73) Assignee: G-8 International Trading Co., LTD, Hiratsuka (JP)

( * ) Notice: Subject to any disclaimer, the term of this patent is extended or adjusted under 35 U.S.C. 154(b) by 0 days.

(21) Appl. No.: 16/092,597

(22) PCT Filed: Nov. 1, 2017

(86) PCT No.: PCT/JP2017/039539
§ 371 (c)(1),
(2) Date: Oct. 10, 2018

(87) PCT Pub. No.: WO2019/043961
PCT Pub. Date: Mar. 7, 2019

(65) Prior Publication Data
US 2021/0053887 A1    Feb. 25, 2021

(30) Foreign Application Priority Data

Aug. 31, 2017  (JP) .............................. JP2017-166386
Oct. 31, 2017  (JP) .............................. JP2017-210353

(51) Int. Cl.
*C05F 11/06*  (2006.01)
*C05G 5/23*   (2020.01)
(Continued)

(52) U.S. Cl.
CPC ................. *C05F 11/06* (2013.01); *B01J 3/02* (2013.01); *B01J 3/03* (2013.01); *B01J 3/04* (2013.01);
(Continued)

(58) Field of Classification Search
None
See application file for complete search history.

(56) References Cited

U.S. PATENT DOCUMENTS 6,695,892 B1 *   2/2004  Fischer et al. .......... C05F 11/02
2009/0314700 A1  12/2009  Mabuchi
(Continued)

FOREIGN PATENT DOCUMENTS

DE    3235452    *   3/1984    .............. C05F 11/00
EP    0004632    *   10/1979   .............. C05F 11/00
(Continued)

OTHER PUBLICATIONS

International Search Report (in Japanese—English translation not yet published) (PCT/JP2017/039539) (3 pages—dated Jan. 30, 2018).
(Continued)

*Primary Examiner* — Wayne A Langel
(74) *Attorney, Agent, or Firm* — Renner, Kenner, Greive, Bobak, Taylor & Weber

(57) ABSTRACT

The fulvic acid solution production method of the present invention comprises: an apparatus preparation step of preparing a processing apparatus which comprises: a hermetic container internally having a closeable processing space; a steam jetting device operable to jet high-temperature and high-pressure steam into the hermetic container; a supply section having an opening-closing mechanism and operable to supply a raw material into the hermetic container; and a discharge section having an opening-closing mechanism and operable to discharge, to the outside, a processed liquid produced through processing of the raw material by the steam; a raw material input step of inputting a raw material containing chips of wood as a primary raw material, from the supply section into the processing space of the hermetic container of the processing apparatus; a stream introduction
(Continued)

step of introducing steam having a temperature of 120 to 250° C. and a pressure of 12 to 35 atm into the processing space in which the raw material is input; a processing step of subjecting the raw material to a subcritical water reaction processing, under stirring, while introducing the steam; a mixed solution obtaining step of cooling the processed raw material after the processing step to obtain a mixed solution containing fulvic acid and humic acid; and a fulvic acid solution taking-out step of separating humic acid and fulvic acid from the obtained mixed solution to take out a fulvic acid solution.

22 Claims, 2 Drawing Sheets

(51) Int. Cl.
| | |
|---|---|
| *B01J 3/02* | (2006.01) |
| *B01J 3/03* | (2006.01) |
| *B01J 3/04* | (2006.01) |
| *C07C 51/42* | (2006.01) |
| *C05F 11/00* | (2006.01) |
| *C07C 51/00* | (2006.01) |
| *C05F 11/02* | (2006.01) |

(52) U.S. Cl.
CPC .............. *C05F 11/00* (2013.01); *C05F 11/02* (2013.01); *C05G 5/23* (2020.02); *C07C 51/00* (2013.01); *C07C 51/42* (2013.01)

(56) References Cited

U.S. PATENT DOCUMENTS

2012/0279266 A1* 11/2012 Van Dyke et al. ..... C05F 11/02
2017/0114276 A1* 4/2017 Spittle et al. ............ C05G 3/04

FOREIGN PATENT DOCUMENTS

| JP | 2-289481 | * 11/1990 | ............. C05C 11/00 |
|---|---|---|---|
| JP | 5-66199 B2 | 9/1993 | |
| JP | 2009-254243 A | 11/2009 | |
| JP | 2014-144440 A | 8/2014 | |
| JP | 6007446 B | 10/2016 | |
| JP | 2017-112947 A | 6/2017 | |
| KR | 10-1723813 B1 | 4/2017 | |

OTHER PUBLICATIONS

Translation of: Mamoru Uchimizu "Nature and Samsara—Soil Nature Human Beings Society—Basic Theory of Civilization", pp. 18-21.

Mamoru Uchimizu "Shizen to Rinne Tsuchi Shizen Ningen Shakai Basic Bunmei-Ron (Nature and Rinne Earth Nature Human Society Basic civilization theory)" pp. 18-28, Manga-sha, 1986.

Translation of cited parts of Cited reference 2: Miyashiro Tomonao: Multi-purpose resources and safety assessment of waste using subcritical water reaction, University of Tsukuba Doctor (Academic) dissertation, 2012.

Miyashiro Tomonao: Multi-purpose resources and safety assessment of waste using subcritical water reaction, University of Tsukuba Doctor (Academic) dissertation, 2012.

Translation of cited parts of Cited reference 3: Jun Matsushita et al., Application of subcritical water technology to restoration of reginal vitality, Japan Society of Defense Facility Engineers (JSDFE) H27 Annual Research Presentaiton (Feb. 2016).

Jun Matsushita et al., Application of subcritical water technology to restoration of reginal vitality, Japan Society of Defense Facility Engineers (JSDFE) H27 Annual Research Presentaiton (Feb. 2016).

* cited by examiner

[Fig.1]
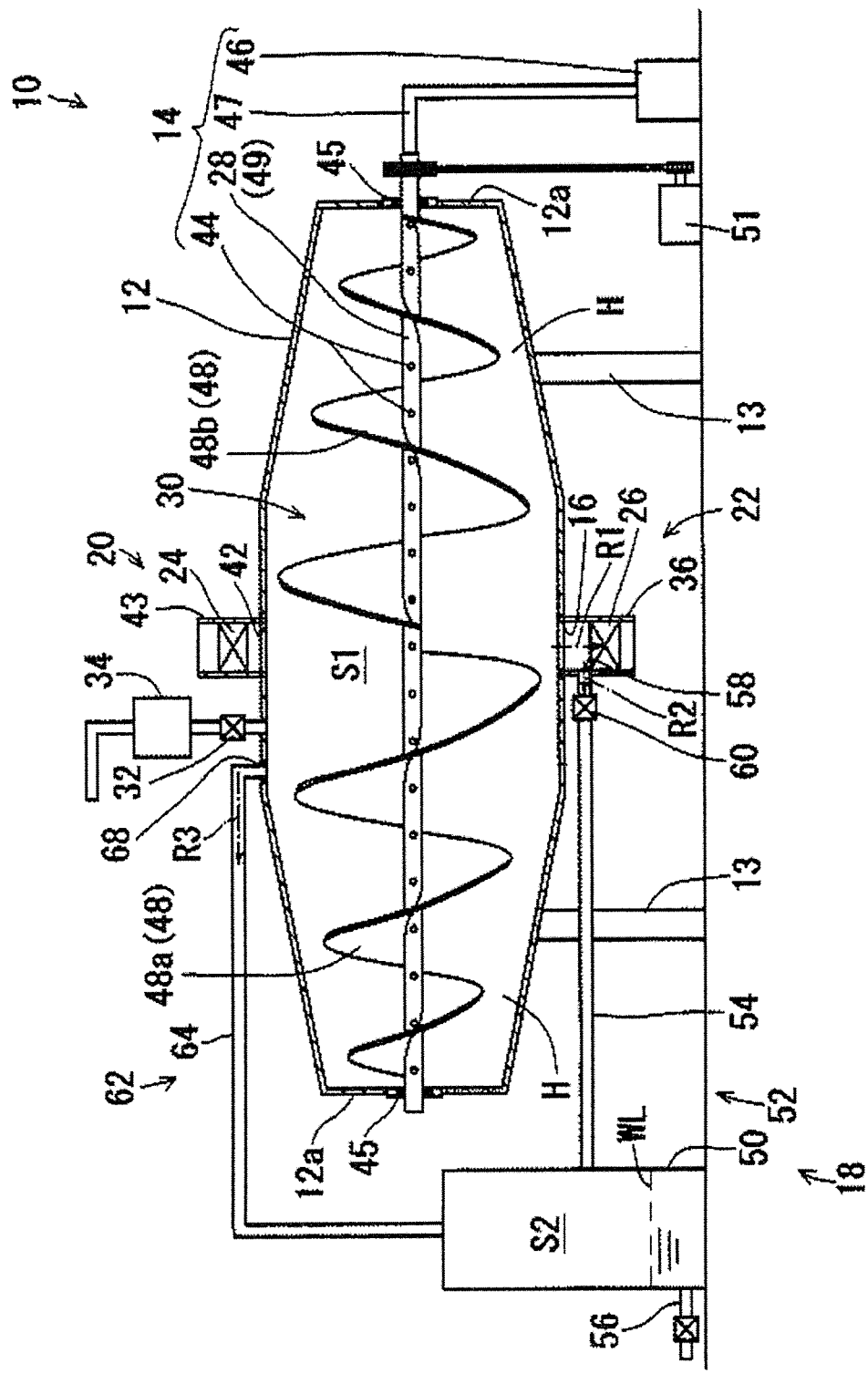

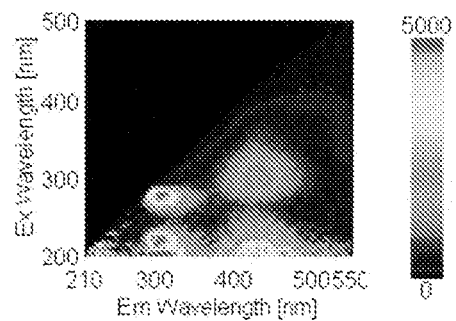
Fig. 2a White birch chips
Alkali solubles
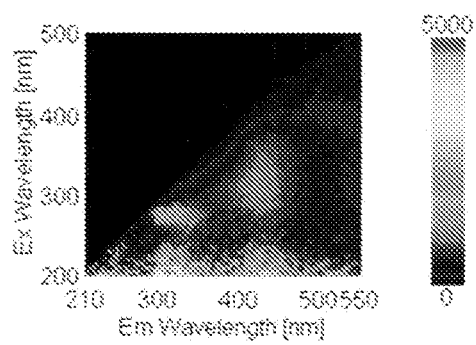
Fig. 2b Willow chips
Alkali solubles
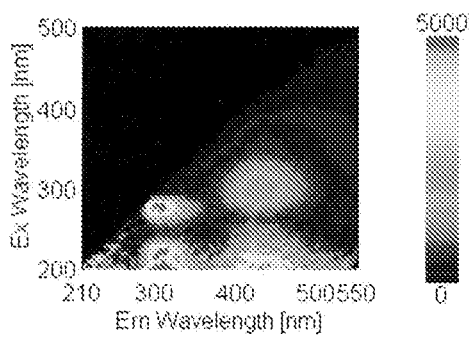
Fig. 2c White birch chips
Fractionated fulvic acid
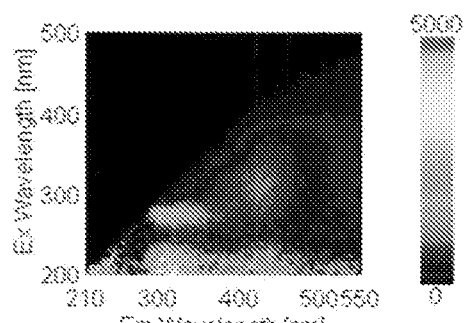
Fig. 2d Willow chips
Fractionated fulvic acid
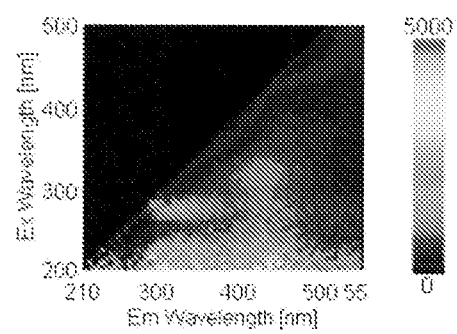
Fig. 2e White birch chips
Fractionated humic acid
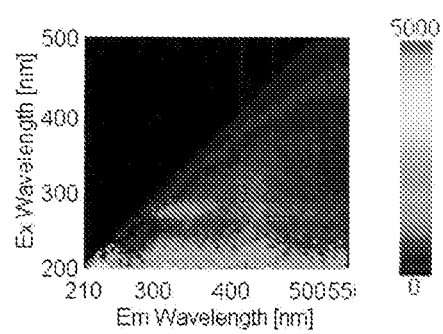
Fig. 2f Willow chips
Fractionated humic acid
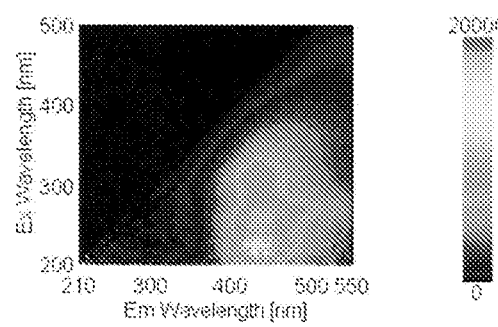
Fig. 2g Standard substance
(Dando fulvic acid (2µg/mL))
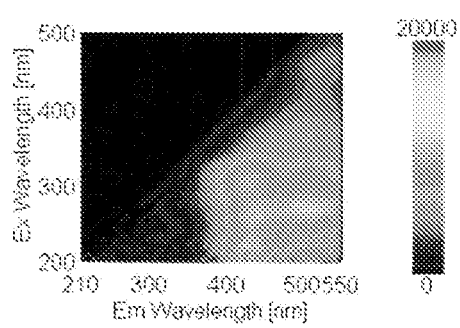
Fig. 2h Standard substance
(Dando humic acid (5µg/mL))

PRODUCTION METHOD FOR FULVIC ACID SOLUTION, AND FULVIC ACID SOLUTION

TECHNICAL FIELD

The present invention relates to a production method for a fulvic acid solution, and a fulvic acid solution produced by the production method.

BACKGROUND ART

"Humic substance" is a generic term used to refer to "organic matters (non-bioorganic matters) whose chemical structures are not specified" derived by breakdown of bio-organic matters by a microbial action and a chemical action, after the death of an organism. This humic substance, as is empirically known, is classified into two types: one exhibiting a functionality; and the other exhibiting no functionality, and this difference is considered to be strongly influenced by whether or not the humic substance contains an intermediate product produced during a process in which bioorganic matter as its initial organic matter in the natural world returns to the soil. When the humic substance contains such an intermediate product, i.e., exhibits a functionality, it is occasionally referred to as "humic substance precursor" (the following Non-Patent Document 1).

A substance equivalent to the humic substance (or the humic substance precursor) has existed in the natural world, and beneficial effects thereof in terms of growth of crops, therapies of diseases and injuries and the like have been utilized in various manners since old times, although it is unclear whether or not it has been recognized as the humic substance. Meanwhile, in recent years, a modern agricultural method and a raw material processing method positively utilizing developed chemical substances have been widely employed. On the other hand, apart from the modern agricultural method and the related raw material processing method, it has been started to reconsider the use of the classically-utilized humic substance, and solutions containing an artificially-produced fulvic acid selectively in high concentrations and the like have been developed and partly placed on the market.

For example, the following Patent Document 1 discloses a technique relating to a wastewater treatment method utilizing, for example, a bacterial group comprising a soil-inhabiting facultative anaerobic bacterium subjected to acclimatization (habituation) culture so as to produce a metabolite including phenol or/and a compound with an exposed phenolic group. The "metabolite including phenol or/and a compound with an exposed phenolic group" can react with a silicic acid component or the like to induce a polycondensation reaction for humification. That is, the Patent Document 1 intends to disclose an excellent wastewater treatment method utilizing humic matter.

As seen in the Patent Document 1 and the Non-Patent Document 1, techniques utilizing a humic substance precursor or a humic substance (humic matter) have been studied. In this connection, it is known that humic matter contains humin, fulvic acid and humic acid, as an indicator of a degree of humification (polycondensation) of components thereof. In a normal humic substance, fulvic acid and humic acid are contained at a weight ratio of about 2:8.

Heretofore, fulvic acid, humic acid and others contained in a humic substance have not been considered as pure substances but as a group of a plurality of organic compounds, and further there has been difficulty in separating them from each other. Thus, although there has been known a technique of using a substance equivalent to such a humic substance, in a treatment process for wastewater containing an organic substance, as disclosed in the Patent Document 1, no sufficient study has been made about what advantage effect each of the substances specifically brings out. However, commercially-available fulvic acid-containing solutions are expected to have effectiveness as a bioactive (microbially active) liquid or the like, and, with a view to promoting utilization in an application field, such as the field of agriculture, requiring to offer a mass-producible inexpensive product, there is a need for a product containing fulvic acid selectively in high concentrations.

Therefore, regarding fulvic acid which is, among humic substances, expected to be utilized as a bioactive (microbially active) liquid, in order to provide a production method for a highly fulvic acid-containing liquid containing fulvic acid at a higher relative ratio with respect to humic acid, as compared to that in a normal humic substance, the following production method was proposed in JP 2017-112947 A (Patent Document 2).

The fulvic acid-containing liquid production method proposed in the Patent Document 2 is characterized in that it comprises: an anaerobically culturing step of culturing an organic substance mixed liquid prepared by mixing an organic substance and fulvic acid-acclimatization (habituation) cultured sludge, for 4 hours or more under the condition that a dissolved oxygen level of the organic substance mixed liquid is set to 0.1 mg-O/L or less, to reduce the organic substance in the organic substance mixed liquid through the anaerobic culture to thereby form an anaerobic culture liquid; an aerobically culturing step of culturing the anaerobic culture liquid, for 6 hours or more under the condition that a dissolved oxygen level of the anaerobic culture liquid is set to 0.2 mg-O/L or more, to increase fulvic acid in the anaerobic culture liquid to thereby obtain a fulvic acid-containing culture liquid; an aerobic culture liquid returning step of returning, to the anaerobically culturing step, a culture liquid before completion of the culture performed in the aerobically culturing step; and a step of obtaining a fulvic acid-containing liquid from the fulvic acid-containing culture liquid obtained from aerobically culturing step.

CITATION LIST

Parent Document

Patent Document 1: JP H05-66199 B
Patent Document 2: JP 2017-112947 A

Non-Patent Document

Non-Patent Document 1: Mamoru UCHIMIZU "Nature and Samsara Soil·Nature·Human Beings·Society Basic Theory of Civilization", pp 18-28, Mangasha Co. Ltd., 1986

SUMMARY OF INVENTION

Technical Problem

It is a primary object of the present invention to provide a fulvic acid solution production method completely different from that described in the above published patent application.

Solution to Technical Problem

The above object is achieved by a fulvic acid solution production method of the present invention and the like having the following features set forth in (1) to (24).

(1) A fulvic acid solution production method comprising: an apparatus preparation step of preparing a processing apparatus which comprises: a hermetic container internally having a closeable processing space; a steam jetting device operable to jet high-temperature and high-pressure steam into the hermetic container; a supply section having an opening-closing mechanism and operable to supply a raw material into the hermetic container; and a discharge section having an opening-closing mechanism and operable to discharge, to the outside, a processed liquid produced through processing of the raw material by the steam; a raw material input step of inputting a raw material containing chips of wood as a primary raw material, from the supply section into the processing space of the hermetic container of the processing apparatus; a processing step of subjecting the raw material to a subcritical water reaction processing, under stirring, while introducing steam having a temperature of 120 to 250° C. and a pressure of 12 to 35 atm into the processing space in which the raw material is input, to obtain a mixed solution containing fulvic acid, humic acid, and suspended matter of chips of wood and/or fragments thereof; and a fulvic acid solution taking-out step of separating fulvic acid from the obtained mixed solution to take out a fulvic acid solution.

(2) In the fulvic acid solution production method set forth in (1), the wood is a felled timber or wood scrap.

(3) In the fulvic acid solution production method set forth in (2), the felled timber is obtained from a broad-leaved tree or a needle-leaved tree.

(4) In the fulvic acid solution production method set forth in (3), the broad-leaved tree is at least one selected from the group consisting of white birch (*Betula platyphylla*), willow (*Salicaceae*), chestnut tree (*Castanea crenata*), oak (*Quercus*), and beech (*Fagus crenata*).

(5) In the fulvic acid solution production method set forth in (3), the needle-leaved tree is at least one selected from the group consisting of pine (*Pinus*), Japanese cedar (*Cryptomeria japonica*), Japanese cypress (*Chamaecyparis obtusa*), and Hiba (*Thujopsis dolabrata*).

(6) In the fulvic acid solution production method set forth in (2), the wood scrap is solid wood or plywood.

(7) In the fulvic acid solution production method set forth in any one of (1) to (6), the processing step is performed for 1 to 8 hours.

(8) In the fulvic acid solution production method set forth in (3), the primary raw material is a broad-leaved tree, and wherein the pressure of steam to be introduced in the processing step is in the range of 12 to 25 atm.

(9) In the fulvic acid solution production method set forth in (3), the primary raw material is a needle-leaved tree, and wherein the pressure of steam to be introduced in the processing step is in the range of 20 to 35 atm.

(10) A fulvic acid solution production method comprising: an apparatus preparation step of preparing a processing apparatus which comprises: a hermetic container internally having a closeable processing space; a steam jetting device operable to jet high-temperature and high-pressure steam into the hermetic container; a supply section having an opening-closing mechanism and operable to supply a raw material into the hermetic container; and a discharge section having an opening-closing mechanism and operable to discharge, to the outside, a processed liquid produced through processing of the raw material by the steam; a raw material input step of inputting a plant raw material comprised of a gramineous plant as a primary raw material, from the supply section into the processing space of the hermetic container of the processing apparatus; a processing step of subjecting the raw material to a subcritical water reaction processing, under stirring, while introducing steam having a temperature of 100 to 200° C. and a pressure of 5 to 25 atm into the processing space in which the raw material is input, to obtain a mixed solution containing fulvic acid and humic acid; and a fulvic acid solution taking-out step of separating fulvic acid from the obtained mixed solution to take out a fulvic acid solution.

(11) In the fulvic acid solution production method set forth in (10), the plant raw material is felled or mowed plant, or a plant scrap.

(12) In the fulvic acid solution production method set forth in (11), the felled or mowed plant is at least one selected from the group consisting of rice (*Oryza sativa*), wheat (*Triticum aestivum*), barley (*Hordeum vulgare*), oat (*Avena fatua*), rye (*Secale cereale*), proso millet (*Panicum miliaceum*), foxtail millet (*Setaria italica*), Japanese millet (*Echinochloa esculenta*), corn (*Zea mays*), finger millet (*Eleusine coracana*), sorghum (*Sorghum bicolor*), bamboo (*Bambusoideae*), manchurian wild rice (*Zizania latifolia*), sugar cane (*Saccharum officinarum*), adlay (*Coix lacryma-jobi* var. ma-yuen), reed (*Phragmites australis*), Japanese silver grass (*Miscanthus sinensis*), arrow bamboo (*Pseudosasa japonica*), giant reed (*Arundo donax*), pampas grass (*Cortaderia selloana*), and lawn grass.

(13) In the fulvic acid solution production method set forth in (11), the felled or mowed plant is rice straw or wheat straw.

(14) In the fulvic acid solution production method set forth in (12), the felled or mowed plant is bamboo.

(15) In the fulvic acid solution production method set forth in (14), the bamboo is formed in a chip shape.

(16) In the fulvic acid solution production method set forth in (10), the raw material is a post-use plant scrap.

(17) In the fulvic acid solution production method set forth in (16), the plant scrap is an aging tatami mat.

(18) In the fulvic acid solution production method set forth in any one of (10) to (17), the processing step is performed for 3 to 30 minutes.

(19) In the fulvic acid solution production method set forth in any one of (1) to (18), the raw material is introduced into the processing space in an amount of 90% by volume or less of the processing space.

(20) In the fulvic acid solution production method set forth in any one of (1) to (18), the raw material is introduced into the processing space in an amount of 50 to 80% by volume of the processing space.

(21) In the fulvic acid solution production method set forth in any one of (1) to (20), the stirring in the processing step is performed by a stirring member rotatably disposed in the processing space.

(22) In the fulvic acid solution production method set forth in any one of (1) to (21), the raw material input step includes adding an alkaline solution as an additive.

(23) A fulvic acid solution produced by the fulvic acid solution production method set forth in any one of (1) to (22).

(24) A substance useful for agriculture and/or stock farming, which includes a solid content produced by the fulvic acid solution production method set forth in any one of (1) to (22).

Effect of Invention

As above, provided is a totally-new fulvic acid solution production method using, as a raw material, wood chips or fragmented pieces of a gramineous plant.

The fulvic acid solution production method of the present invention makes it possible to obtain a high-purity fulvic acid solution.

A solid content after reaction is usable as a substance useful for agriculture and/or stock farming.

BRIEF DESCRIPTION OF DRAWINGS

FIG. 1 is a sectional view depicting one example of a production apparatus for implementing a fulvic acid solution production method according to one embodiment of the present invention.

FIG. 2a is a photographic representation of a three-dimensional excitation-emission matrix fluorescence spectrum of a sample in Example 1.

FIG. 2b is a photographic representation of a three-dimensional excitation-emission matrix fluorescence spectrum of a sample in Example 2.

FIG. 2c is a photographic representation of a three-dimensional excitation-emission matrix fluorescence spectrum of the sample in Example 1.

FIG. 2d is a photographic representation of a three-dimensional excitation-emission matrix fluorescence spectrum of the sample in Example 2.

FIG. 2e is a photographic representation of a three-dimensional excitation-emission matrix fluorescence spectrum of the sample in Example 1.

FIG. 2e is a photographic representation of a three-dimensional excitation-emission matrix fluorescence spectrum of the sample in Example 2.

FIG. 2g is a photographic representation of a three-dimensional excitation-emission matrix fluorescence spectrum of a standard substance.

FIG. 2h is a photographic representation of a three-dimensional excitation-emission matrix fluorescence spectrum of the standard substance.

DESCRIPTION OF EMBODIMENTS

A fulvic acid solution production method of the present invention will now be described based on an embodiment thereof.

First of all, one example of a production apparatus (processing apparatus) 10 for implementing a fulvic acid solution production method according to one embodiment of the present invention will be described.

FIG. 1 is a sectional view of the production apparatus.

The production apparatus 10 comprises: a hermetic container 12 internally having a closeable space S1 capable of containing chips of wood or fragmented pieces of a gramineous plant; a steam jetting device 14 operable to jet, into the hermetic container 12, high-temperature and high-pressure steam which is subcritical water; an outlet port 16 provided at a bottom of the hermetic container 12 and provided with an opening-closing mechanism 26; and a separation-collection device 18 operable to separate and collect liquid from a processed raw material, only by operation of directly discharging the liquid from the outlet port 16. While the hermetic container 12 may have any shape, such as a rectangular box-like shape, a three-dimensional polygonal cylindrical shape, a circular cylindrical shape, a barrel-like shape, or a drum-like shape, it preferably has a shape which enables the liquid to be gravitationally discharged from the outlet port 16 provided in a bottom wall thereof. The lower wall of the hermetic container is preferably provided to extend obliquely downwardly toward the outlet port.

The separation-collection device 18 may comprise: a liquid collection unit 50 having a second closeable space S2 different from the first closeable space S1 of the hermetic container 12 and communicated with an inside of the hermetic container 12 through the outlet port 16; and a gravity flow-based collection mechanism 52 for causing only the liquid in the hermetic container 12 to be collected to the liquid collection unit 50 through the outlet port 16 by gravity flow. The processed raw material as a solid content located around the outlet port 16 remains as-is within the hermetic container 12, and only the liquid gravitationally flows toward the liquid collection unit 50, so that the liquid can be separated and collected from the raw material. As long as the liquid collection unit 50 has the closable space S2 for storing the collected liquid, it may be constructed in any configuration, such as a metal tank, a three-dimensional polygonal housing or a tubular body. The liquid collection unit 50 may be formed plurally.

The gravity flow-based collection mechanism 52 may comprise a pressure equalization device 62 for equalizing pressures of the closeable space S1 of the hermetic container 12 and the closeable space S2 of the liquid collection unit 50. By always equalizing internal pressures of the hermetic container 12 and the liquid collection unit 50, it becomes possible to enable a liquid collection operation to be performed immediately after completion of the processing so as to shorten the operation time.

Although the above production apparatus has been described based on one example in which separation means is incorporated in the processing apparatus, the separation means may be provided separately without providing it in the processing apparatus itself.

Further, a pressure equalization device 62 for equalizing pressures of the closeable space S1 of the hermetic container 12 and the closeable space S2 of the liquid collection unit 50 may be provided. The pressure equalization device 62 may comprise a pressure-equalizing communication pipe 64 for providing fluid communication between the closeable space S1 of the hermetic container 12 and the closeable space S2 of the liquid collection unit 50, to serve as a second path different from a first liquid collection path through the outlet port 16. The pressure-equalizing communication pipe 64 may be configured such that it always provides fluid communication between the closeable space S1 and the closeable space S2 to always keep internal pressures of the hermetic container 12 and the liquid collection unit 50 in an equalized state. As long as the pressure-equalizing communication pipe 64 is capable of providing fluid communication between the hermetic container 12 and the liquid collection unit 50 to equalize pressures thereof, at least before the liquid collection operation, it may be provided with an opening-closing mechanism for setting the pressure-equalizing communication pipe to a communicating state or a non-communication state.

The fluid communication between the pressure-equalizing communication pipe 64 and the hermetic container 50, which forms the second path, may be performed through a communication pipe connection portion 68 provided at an upper end of the hermetic container 12

The gravity flow-based collection mechanism 52 may comprise a liquid collection flow passage 54 for communicatably connecting the outlet port 16 of the hermetic container 12 and the liquid collection unit 50, wherein the liquid collection flow passage 54 is provided to extend horizontally or obliquely downwardly from one end thereof communicated with the outlet port 16 toward the liquid collection unit 50.

Further, an opening-closing mechanism 26 may be provided in the middle of a discharge path R1 extending from the outlet port 16 to discharge the processed raw material, wherein a liquid inlet 58 of the liquid collection flow passage 54 may be communicatably connected to the discharge path R1 at a position upstream of the opening-closing mechanism 26.

The liquid collection flow passage 54 may be provided with an opening-closing mechanism 60 for selectively switching between the communicating and non-communicating states of the flow passage in such a manner as to set the flow passage to the non-communicating state during processing of the raw material within the hermetic container 12, and set the flow passage to the communicating state during the operation of collecting only the liquid after completion of the processing.

The liquid collection unit 50 may be disposed such that a bottom of the closeable space S2 thereof is located at a height position lower than the outlet port 16 of the hermetic container 12.

Further, the liquid collection unit 50 may be configured such that a liquid level WL of the liquid collected within the closeable space S2 thereof is always at a height position lower than the outlet port 16.

The hermetic container 12 may be internally provided with a stirring device 30 for stirring the raw material.

Further, the hermetic container 12 may be formed in a lying barrel-like shape which is provided with the outlet port 16 at a bottom in a longitudinal (in FIG. 1, a rightward-leftward directional) central region thereof and whose diameter is gradually reduced in a direction from the longitudinal central region toward each of longitudinally opposite ends thereof, and the stirring device 30 may comprise: a rotary shaft 49 provided inside the hermetic container 12 to extend longitudinally and supported rotatably and pivotally with respect to the hermetic container 12; and a stirring blade 48 attached onto the rotary shaft 49 and having a region expanding in a circumferential direction of the rotary shaft 49, wherein the stirring blade 48 may be formed such that a length thereof between the rotary shaft 49 and a distal edge thereof is maximized at a longitudinal central position of the rotary shaft 49 and gradually reduced toward each of longitudinally opposite ends of the rotary shaft 49, correspondingly to the lying barrel-like shape of the hermetic container 12.

The steam jetting device 14 may comprise a rotary shaft-cum-steam jetting pipe 28 obtained by preparing the rotary shaft 49 in the form of a hollow pipe, and forming a plurality of steam jetting holes 44 in a peripheral wall of the hollow pipe.

In this example, the hermetic container 12 is supported by a support leg 13 such that it is disposed at a certain height position above the ground. The hermetic container 12 is formed in a lying barrel-like shape whose diameter is gradually reduced in a direction from the longitudinal central region toward each of two end walls 12a at the longitudinally opposite ends thereof. For example, the hermetic container 12 is formed by processing a metal plate to exhibit heat resistance and pressure resistance and have a size enough to contain the raw material in a volume of about 2 $m^3$. The hermetic container 12 has an input section 20 and a discharge section 22 which are provided, respectively, on an upper side of the central region thereof and on a lower side of the central region thereof, and configured to be selectively opened and closed, respectively, by an opening-closing mechanism 24 and an opening-closing mechanism 26. The closeable space S1 of the hermetic container 12 is provided with therein an aftermentioned steam jetting pipe 28 constituting the steam jetting device 14, and a stirring device 30 for stirring the raw material. The hermetic container 12 is provided with a safety valve 32 operable, when the internal pressure becomes greater than a setup value, to relieve internal steam, e.g., capable of adjusting the setup value. Further, a sound-deadening and odor-eliminating device 34 is provided in the middle of a relief pipe connected to the safety valve 32, so that steam relieved via the safety valve 32 is subjected to sound-deadening and odor-eliminating, and then discharged toward the external air.

As shown, the outlet port 16 is opened in a bottom wall of the longitudinal central region of the hermetic container 12, in such a manner that the processed raw material is discharged downwardly. The outlet port 16 is formed to have a diameter, for example, of about 300 mm A cylindrical discharge sleeve 36 protruding downwardly is connected to the outlet port 16 to form a processed raw material discharge path R1, and the opening-closing mechanism 26 is provided in the middle of the discharge path R1 so as to selectively open and close the outlet port 16. That is, the discharge section 22 is constructed such that it comprises the outlet port 16, the discharge sleeve 36 and the opening-closing mechanism 26. The hermetic container 12 is formed in a lying barrel-like shape, so that it becomes possible to facilitate enabling the internal raw material to gravitationally gather toward the central region provided with the outlet port 16, and to discharge the processed raw material via the outlet port 16 simply by opening the opening-closing mechanism 26.

In the input section 20, an input port 42 is opened in a top wall of the hermetic container 12, and a cylindrical input sleeve 43 protruding upwardly is connected to the input port 42. The opening-closing mechanism 24 is composed, for example, of a ball valve, and provided inside the input sleeve 43 so as to selectively open and close the input sleeve 43. When the opening-closing mechanism 24 is opened, the input port 42 is opened to enable the raw material to be input therethrough. On the other hand, when the opening-closing mechanism 24 is closed, the closable space S1 of the hermetic container 12 is maintained in a closed state.

The steam jetting device 14 is operable to jet high-temperature and high-pressure steam into the hermetic container 12 to set the inside of the hermetic container 12 to a high-temperature and high-pressure state and thus process the raw material through the steam. As depicted in FIG. 1, the steam jetting device 14 comprises: a steam jetting pipe 28 disposed within the hermetic container 12 and composed of a hollow pipe having a peripheral wall formed with a large number of steam jetting holes 44; a steam generator 46 such as a boiler; and a steam delivery pipe 47 for delivering steam from the steam generator 46 into the steam jetting pipe 28. In order to adequately process the raw material, steam to be jetted from the steam jetting device 14 into the hermetic container 12 is set at a high temperature and a high pressure which are equivalent to those of subcritical water. For example, steam to be jetted from the steam jetting pipe 28 is set at a temperature of about 100 to 250° C. and a pressure of about 5 to 35 atm. As a result, the inside of the hermetic container 12 is set at a temperature of about 100 to 250° C. and a pressure of about 5 to 35 atm. The steam jetting pipe 28 is disposed to extend horizontally at an approximately central position in an upward-downward direction of the hermetic container 12, and supported rotatably and pivotally by the end walls 12a through bearings 45. That is, the steam jetting pipe 28 is configured to radially jet steam while being rotated about a horizontal axis thereof, to thereby apply steam directly to the raw material. The steam jetting pipe 28 is configured to be rotated by rotational drive force obtained from a rotational drive unit 51 such as a motor through a chain or the like. Further, the steam jetting pipe 28 is mounted with the stirring blade 48 constituting the stirring device, to additionally serve as the rotary shaft 49 of the stirring device. That is, in this embodiment, the steam jetting device 14 comprises a rotary shaft-cum-steam jetting pipe 28 obtained by preparing the rotary shaft 49 of the stirring device in the form of a hollow pipe, and forming a plurality of steam jetting holes in a peripheral wall of the hollow pipe. It should be noted that the steam jetting device is not limited to this configuration, but may have any other suitable configuration, such as a configuration in which steam is jetted from a distal end of a pipe inserted into the hermetic container, or a configuration in which a plurality of the steam jetting pipes are arranged within the hermetic container.

The stirring device 30 is provided as a means to stir the raw material to be processed in the hermetic container, so as to process the raw material evenly and promptly. The stirring device 30 comprises a rotary shaft 49 composed of the steam jetting pipe 28, and a stirring blade 48 attached onto the rotary shaft 49 and having a region expanding in a circumferential direction of the rotary shaft 49. In this embodiment, the stirring blade 48 is composed of a right-handed helical blade 48a and a left-handed helical blade 48b which are provided such that helical directions thereof are inverted at an approximately axial central position of the rotary shaft 49. The stirring blade 48 is formed such that a length thereof between the rotary shaft and a distal edge thereof is gradually reduced from a longitudinal central position of the rotary shaft toward each of the longitudinally opposite ends of the rotary shaft. This makes it possible to reliably stir the raw material, correspondingly to the lying barrel-like shape of the hermetic container 12. Further, the stirring blade 48 is disposed such that a certain amount of gap H is formed between the distal edge of the blade and an inner wall surface of the hermetic container 12. The helical blades 48a, 48b are capable of stirring the raw material while conveying the raw material from the central region toward the end walls of the hermetic container and breaking the solid-form raw material. The raw material conveyed to the end walls 12a by the stirring blade 48 is pushed by a raw material subsequently conveyed to the end walls 12a, and returned to the central region through the gap H along the inner wall surface of the hermetic container 12. It should be understood that the stirring device 30 is not limited to the above configuration, but may have any other suitable configuration.

The separation-collection device 18 is provided as means to, after completion of the steaming, separate and collect liquid from the processed raw material in the hermetic container 12, only by operation of directly discharging the liquid from the outlet port. As depicted in FIG. 1, the separation-collection device 18 comprises: a liquid collection unit 50 communicated with the inside of the hermetic container 12 through the outlet port 16; and a gravity flow-based collection mechanism 52 for causing the liquid to be collected to the liquid collection unit 50 through the outlet port 16 by gravity flow.

The liquid collection unit 50 is a second hermetic container internally having a second closeable space S2 different from the first closeable space S1 of the hermetic container 12. For example, the liquid collection unit 50 is composed of a metal cylindrical-shaped hermetic tank having heat resistance and pressure resistance. The liquid collection unit 50 is communicatably connected to the outlet port 16 of the hermetic container 12 via a liquid collection flow passage 54 formed, for example, of a metal pipe member. The liquid collection unit 50 is disposed such that a bottom of the closeable space S2 thereof is located at a height position lower than the outlet port 16 of the hermetic container 12, and a liquid level WL of the liquid collected within the closeable space S2 is always at a height position lower than the outlet port 16, whereby the liquid around the outlet port is easy to gravitationally flow toward the liquid collection unit in a smooth manner. The liquid collection unit 50 is provided with a drain 56 for extracting the collected liquid. The drain 56 is configured to be selectively opened and closed by an on-off valve.

The gravity flow-based collection mechanism 52 is provided as a means to enable only liquid accumulated in the hermetic container 12 to flow from the outlet port to the liquid collection unit 50 by gravity flow. The gravity flow-based collection mechanism 52 comprises the liquid collection flow passage 54, wherein the liquid collection flow passage 54 has an liquid inlet 56 communicatably connected to the outlet port 16, and forms a liquid collection path R2 branched from the processed raw material discharge path R1. In this embodiment, the liquid collection flow passage 54 is composed, for example, of a metal pipe having an inner diameter of about 6 mm. The liquid collection flow passage 54 is provided with an opening-closing mechanism 60 for selectively switching between the communicating and non-communicating states of the flow passage. The opening-closing mechanism 60 is switched in such a manner as to set the flow passage to the non-communicating state during processing of the raw material within the hermetic container 12, and set the flow passage to the communicating state during the operation of collecting only the liquid after completion of the processing. Thus, as well as the raw material, liquid derived from liquefaction of moisture or vapor contained in the raw material, with bacteria and malodorous components contained in the raw materials, can be processed by the high-temperature and high-pressure stream. Therefore, after completion of the processing, the liquid can be separated and collected in a state after destroying bacteria, and decomposing malodorous and harmful components, etc., and it is not necessary to secondarily process the separated and collected liquid, thereby to shorten the time without labor.

The liquid inlet 58 of the liquid collection flow passage 54 is communicatably connected to the processed raw material drain path R1 at a position upstream of the opening-closing mechanism 26. Thus, the liquid is separated and collected through the outlet port by closing the opening-closing mechanism 26 of the outlet port 16, and, in this state, opening the opening-closing mechanism 60 of the liquid collection flow passage 54 to set the liquid collection flow passage to the communicating state. The liquid collection flow passage 54 is connected to the discharge sleeve 36 in orthogonal relation, i.e., the liquid collection path R2 is provided in orthogonal relation to the processed raw material discharge path R1. That is, in the closed state of the opening-closing mechanism 26, the liquid flows in a direction intersecting with a direction along which a deposition pressure of the processed raw material in the hermetic container is applied. This makes it less likely for the processed raw material to enter the liquid inlet 58, in a simplified structure, so that it becomes possible to enable only the liquid through to gravitationally flow through the liquid collection flow passage 54 so as to perform good separation and collection of the liquid. If momentum of a flow of the liquid from the hermetic container 12 into the liquid inlet 58 is excessively strong, the processed raw material is likely to flow into the liquid inlet 58 together with the liquid by a flow force of the liquid. Thus, a connection structure with the liquid collection flow passage, the liquid inlet 58 or the like is preferably configured to form a flow which is gentle enough not to carry the processed raw material. The liquid collection flow passage 54 is provided to extend generally horizontally from one end (liquid inlet) communicated with the outlet port 16 toward the liquid collection unit. Thus, the liquid smoothly flows through the liquid collection flow passage, and gravitationally flows from the outlet port to the liquid collection unit. The liquid collection flow passage 54 may be disposed obliquely downwardly toward the liquid collection unit, to enable the liquid to more smoothly flow through the liquid collection flow passage 54. In this case, for example, the liquid collection flow passage 54 may be configured such that a part thereof on the side of the liquid inlet 58 extends horizontally by a certain length from the liquid inlet 58, and the remaining part extends obliquely downwardly. The liquid inlet 58 may be provided with a filter or the like, as needed.

Further, as depicted in FIG. 1, the gravity flow-based collection mechanism 52 comprises a pressure equalization device 62 for equalizing pressures of the closeable space S1 of the hermetic container 12 and the closeable space S2 of the liquid collection unit 50. In a normal operation, the inside of the hermetic container 12 after completion of the processing has a relatively high pressure. Thus, in the liquid collection flow passage, a pressing force acts toward the closable space S2 of the liquid collection unit having an internal pressure less than the inside of the hermetic container 12, due to a pressure difference therebetween. Under action of such a pressing force, the processed raw material is liable to flow into the liquid collection flow passage 54 together with the liquid, so that it becomes difficult to separate and collect the liquid from the processed raw material, and the liquid collection flow passage is highly likely to be clogged with the processed raw material. In this embodiment, in advance of the liquid collection operation, pressures of the two closeable spaces S1, S2 of the hermetic container 12 and the liquid collection unit 50 can be equalized by the pressure equalization device 62. This makes it possible to prevent the processed raw material from forcedly flowing into the liquid collection flow passage due to the pressure difference between the two closeable spaces S1, S2, and thus appropriately collect the liquid to the liquid collection unit while separating the liquid from the processed raw material, by means of gravity flow. Further, the separation and collection operation can be performed even when the inside of the hermetic container after completion of the processing is in a high-pressure state, so that it becomes possible to shorten a time required for the operation.

The pressure equalization device 62 comprises a pressure-equalizing communication pipe 64 for providing fluid communication between the closeable space S1 of the hermetic container 12 and the closeable space S2 of the liquid collection unit 50, to serve as a path R3 different from the liquid collection path R2 (liquid collection flow passage 54) through the outlet port 16. For example, the pressure-equalizing communication pipe 64 is composed of a metal pipe, and capable of equalizing the pressures of the two closeable spaces S1, S2 efficiently and in a simplified structure. In FIG. 1, the pressure-equalizing communication pipe 64 has one end communicatably connected to the upper end of the longitudinal center region of the hermetic container 12, and the other end communicatably connected to an upper end of the liquid collection unit 50. The fluid communication between the pressure-equalizing communication pipe 64 and the hermetic container 12, which forms the path R3, may be performed through a communication pipe connection portion 68 provided at an upper end of the hermetic container 12. The communication pipe connection portion 68 is configured such that a connection port thereof is opened downwardly with respect to the hermetic container. Thus, the processed raw material accumulated in the hermetic container 12 is less likely to enter the pressure-equalizing communication pipe 64, so that it becomes possible to prevent the pressure-equalizing communication pipe 64 from being clogged with the processed raw material so as to maintain a communicating state of the pressure-equalizing communication pipe, and thus reliably equalize internal pressures of the hermetic container 12 and the liquid collection unit 50. The pressure-equalizing communication pipe 64 is always in the communicating state, and, when the opening-closing mechanism 60 of the liquid collection flow passage 54 is in a closed state, the hermetic container 12, the liquid collection unit 50 and the liquid collection flow passage 54 are set in a pressure-equalized state. This makes it possible to prevent the processed raw material around the outlet port 16 from forcedly flowing into the liquid inlet 58 due to the pressure difference, even just after opening the opening-closing mechanism 60 of the liquid collection flow passage 54. Further, when collecting the liquid while maintaining the opening-closing mechanism 60 in the open state, the hermetic container 12 and the liquid collection unit 50 are always kept in the pressure-equalized state. Thus, the pressure-equalized state is maintained in the period before the collection through until completion of the collection, so that it become possible to enable only the liquid to be appropriately separated and collected from the outlet port 16 by gravity flow. It should be understood that the pressure equalization device 62 is not limited to this configuration, but may have any other suitable configuration. For example, the pressure equalization device 62 may be provided with an additional high-pressure forming unit for setting the inside of the liquid collection unit to a high pressure, and configured to monitor the internal pressure of the hermetic container by a sensor, and adjust the internal pressure of the liquid collection unit so as to equalize respective internal pressures of the liquid collection unit and the hermetic container. Alternatively, the internal pressure of the hermetic container may be reduced.

Next, a fulvic acid solution production method according to one embodiment of the present invention, using the above production apparatus 10, will be described.

The fulvic acid solution production method according to this embodiment comprises; an apparatus preparation step of preparing the aforementioned processing apparatus; a raw material input step of inputting a raw material containing, as a primary raw material, chips of wood or fragmented pieces of a gramineous plant, from the supply section into the processing space of the hermetic container of the processing apparatus; a processing step of subjecting the raw material to a hydrothermal reaction processing, under stirring, while introducing steam having a temperature of 120 to 250° C.

and a pressure of 12 to 35 atm when the raw material is the wood chips, or having a temperature of 100 to 200° C. and a pressure of 5 to 25 atm when the raw material is the fragmented pieces of the gramineous plant, into the processing space in which the raw material is input, to obtain a mixed solution containing fulvic acid and humic acid; and a fulvic acid solution taking-out step of separating fulvic acid from the obtained mixed solution to take out a fulvic acid solution.

The above steps will be described in detail below.

«Apparatus Preparation Step»

Referring to the drawings, the aforementioned production apparatus (processing apparatus) is prepared.

«Raw Material Input Step»

The raw material may comprise chips of wood as a primary raw material. Preferably, the chip has a long side of about 5 to 150 cm and a short side of about 2 to 5 cm. With a view to efficiently producing a larger amount of fulvic acid, it is possible to add an alkaline solution, as a secondary material or additive. The pressure and temperature of the steam in the case of adding an alkaline solution may be the same as those in the case of adding no alkaline solution.

Generally, as the wood, it is possible to use a felled timber or wood scrap.

The felled timber may be obtained from a broad-leaved tree or a needle-leaved tree.

While the broad-leaved tree may be any type of broad-leaved tree, it has been verified so far that at least the following broad-leaved trees can be desirably used: white birch (*Betula platyphylla*), willow (*Salicaceae*), chestnut tree (*Castanea crenata*), oak (*Quercus*), and beech (*Fagus crenata*).

It has been verified so far that at least the following needle-leaved tree can be desirably used: pine (*Pinus*), Japanese cedar (*Cryptomeria japonica*), Japanese cypress (*Chamaecyparis obtusa*), and Hiba (*Thujopsis dolabrata*).

When a felled timber is used, it is not necessary to remove bark, leaves or the like.

Examples of the wood scrap include wood waste arising from demolition of a wooden building (square log, board: solid wood, laminated wood or plywood (veneer board)). This wood waste is generally formed into chips, so that the resulting wood chips can be directly used as the raw material.

The above raw materials may be used in the form of a mixture. For example, when tree felling is performed in general household, various types of felled timbers are generated. These felled timbers may be directly formed into chips in the form of a mixture, without sorting them, to thereby obtain the raw material. It is to be understood that chips of the wood scrap may be mixed with the wood chips.

The raw material may comprise, as a primary raw material, fragmented pieces of stalk (stem) or branch of a gramineous plant, specifically, in the case of rice (*Oryza sativa*), wheat (*Triticum aestivum*) or the like, fragmented pieces of chaff, leaf or the like thereof, or in the case of bamboo (*Bambusoideae*), arrow bamboo (*Pseudosasa japonica*) or the like, fragmented pieces of stalk or leaf thereof. The length of the fragmented piece is preferably set to 400 mm or less, particularly preferably in the range of 50 to 200 mm. If the length is increased beyond the above upper limit, it becomes difficult to input the fragmented pieces into the processing space, or the fragmented pieces are likely to wind around the stirring member, thereby leading to deterioration in production capability. Even if the length is set to be less than the above lower limit, it poses no problem on the processing for producing fulvic acid. However, it needs to take time and effort for fragmentation. With a view to efficiently producing a larger amount of fulvic acid, it is possible to add an alkaline solution, as a secondary material or additive. The pressure and temperature of the steam in the case of adding an alkaline solution may be the same as those in the case of adding no alkaline solution.

The plant raw material may be an aging tatami mat.

Examples of the gramineous plant include rice (*Oryza sativa*), wheat (*Triticum aestivum*), barley (*Hordeum vulgare*), oat (*Avena fatua*), rye (*Secale cereale*), proso millet (*Panicum miliaceum*), foxtail millet (*Setaria italica*), Japanese millet (*Echinochloa esculenta*), corn (*Zea mays*), finger millet (*Eleusine coracana*), sorghum (*Sorghum bicolor*), bamboo (*Bambusoideae*), manchurian wild rice (*Zizania latifolia*), sugar cane (*Saccharum officinarum*), adlay (*Coix lacryma-jobi* var. ma-yuen), reed (*Phragmites australis*), Japanese silver grass (*Miscanthus sinensis*), arrow bamboo (*Pseudosasa japonica*), giant reed (*Arundo donax*), pampas grass (*Cortaderia selloana*), and lawn grass.

The aforementioned chip-form raw material is input into the processing space. In this process, the raw material is preferably input in an amount of 90% or less, particularly preferably in an amount of 50 to 80%, of the processing space, i.e., the closable space S1 of the hermetic container 12. If the input amount of the raw material is less than the above lower limit, it leads to poor processing efficiency. On the other hand, if the input amount is greater than the above upper limit, there is a possibility that steam fails to adequately act on the raw material, resulting in insufficient production of fulvic acid.

«Processing Step»

In this step, steam is introduced into the processing space in which the raw material is input. This steam is set to have a temperature of 120 to 250° C. and a pressure of 12 to 35 atm when the raw material is wood chips, or to have a temperature of 100 to 200° C. and a pressure of 5 to 25 atm when the raw material is a gramineous plant. Although a preferred volume of steam to be introduced varies depending on the volume of the processing space and the volume of the raw material to be processed, it is preferably set to allow a remaining space (value obtained by subtracting the volume of the input raw material from the volume of the processing space) to be fully filled therewith.

When the raw material is a woody plant, wherein a broad-leaved tree is used as the felled timber, the pressure of the stream during the processing step is preferably set in the range of 12 to 25 atm.

Similarly, when a needle-leaved tree is used as the felled timber, the pressure of the stream during the processing step is preferably set in the range of 12 to 25 atm.

In the processing step, steam is introduced into the processing space in which the raw material is input, and, in this state, the raw material is subjected to processing based on a subcritical water reaction, under stirring, as mentioned above.

The processing step is performed for 20 minutes to 12 hours when the raw material is a woody plant, or for 3 to 34 minutes when the raw material is a gramineous plant. If the processing time is less than the above lower limit, a reaction time becomes insufficient, i.e., the production of fulvic acid becomes insufficient, so that a substantial amount of fulvic acid will remain in the raw material. On the other hand, if the processing time is greater than the above upper limit, the raw material is undesirably carbonized, and is no longer a substance useful for agriculture and/or stock farming.

A preferred internal temperature and pressure of the processing space during the processing step vary depending on a type and state of the raw material to be used. Specifically, the inside of the processing space during the processing step is maintained at a pressure of 120 to 250° C. and a pressure of 12 to 35 atm when the raw material is a woody plant, or at a pressure of 100 to 200° C. and a pressure of 5 to 25 atm when the raw material is a gramineous plant.

Through the processing step, the raw material is subjected to the subcritical water reaction processing, to obtain a solution containing fulvic acid and humic acid. This solution also contains suspended matter of wood chips and/or fragments thereof. That is, a mixed solution containing fulvic acid, humic acid, and suspended matter of wood chips and/or fragments thereof is obtained.

In the mixed solution obtained in the processing step, with respect to a total amount (solid content) of fulvic acid and humic acid, fulvic acid is contained in an amount of 3 to 12% when the raw material is a woody plant, or in an amount of 2 to 10% when the raw material is a gramineous plant.

«Cooling Step»

After completion of the processing step, a cooling step may be performed. In this cooling step, the processing space is cooled, i.e., the steam in the processing space is cooled to obtain a solution containing fulvic acid and humic acid. Generally, this cooling is performed by natural cooling.

«Fulvic Acid Solution Taking-Out Step»

In the fulvic acid solution taking-out step, fulvic acid and humic acid are separately taken out from the mixed solution obtained in the precedent step (the processing step or a combination of the processing step and the cooling step), to obtain a fulvic acid solution.

The separation between fulvic acid and humic acid in the fulvic acid solution taking-out step is performed by separating humic acid by means of precipitation caused by adjusting the mixed solution to exhibit an acidic pH, or by separating humic acid by means of filtration.

The pH value of the mixed solution is preferably set to 2 to 3.

EXAMPLES

First of all, a processing apparatus having the structure as depicted in FIG. 1 was prepared, wherein the volume of the processing space in the hermetic container was 2 m$^3$.

An experimental test of production of a fulvic acid solution was performed by preparing, as the raw material, chips of a felled timber of white birch (Example 1) and chips of a felled timber of willow (Example 2), and inputting each of the raw materials into the processing space. In each of Examples 1 and 2, the wood chip has a long side of about 10 cm on average. In each of Examples 1 and 2, an input amount of the raw material was set to 1.6 m$^3$ (80% of the volume of the processing space). After input of the raw material, the raw material was subjected to a subcritical water reaction processing, under stirring by a stirring device, while introducing steam having a temperature of 250° C. and a pressure of 25 atm into the processing space. In each of Examples 1 and 2, a processing time was set to 1 hour.

In a holding period in the processing step, the inside of the processing space during the processing step was kept at a temperature of 250° C. and a pressure of 25 atm.

After completion of the processing, the processing space was communicated with atmospheric air to set the processing space to atmospheric pressure. Subsequently, only a mixed solution was extracted from the processing apparatus.

Subsequently, the mixed solution in each of Examples 1 and 2 was analyzed in the following manner to check the presence of fulvic acid and others. A result of the analysis is presented in the following Table 1 to 5.

Analytical Items

Total organic carbon (TOC): JIS K 0102(2016) 22.1 Combustion oxidation-infrared TOC analysis method Humic substance (quantitative determination of fulvic acid and humic acid): Three-dimensional fluorescence spectrophotometry Analysis Method 1) Extraction of Alkali Solubles A sample was put in a centrifuge tube, and subjected to centrifugal separation at 3000 rpm for 10 minutes. A resulting supernatant was neutralized using NaOH. Then, a NaOH solution was further added thereto to become equivalent to a 0.1M-NaOH solution, and alkali solubles were extracted. The resulting solution was filtered by a GF/F filter, and a resulting filtrate was used as a sample liquid.

2) Fractionation of Fulvic Acid and Humic Acid

The sample liquid prepared in the step 1) was subjected to fractionation, based on the following definition.

<Definition of Fractionation of Humic Substance>

In each of Examples 1 and 2, when a sample is alkalified using a NaOH solution, and after filtrating the alkalified solution, hydrochloric acid is added to the filtrated solution to acidify the filtrated solution, a resulting precipitate is defined as humic acid, and a substance remaining in the acidified solution is defined as fulvic acid.

Measurement of TOC

Each of the sample liquid extracted in the step 1) and the fulvic acid and humic acid solutions fractionated in the step 2) was subjected to measurement of TOC.

Measurement of Three-Dimensional Fluorescence Spectrum

Each of the sample liquid extracted in the step 1) and the fulvic acid and humic acid solutions fractionated in the step 2) was subjected to measurement of three-dimensional fluorescence spectrum. The measurement was performed at an excitation wavelength (Ex) of 200 to 500 nm and a fluorescence wavelength (Em) of 210 to 550 nm. Then, based on a sum of fluorescence intensities in a wavelength band in which a humic substance produces fluorescence, derived from the obtained three-dimensional fluorescence spectrum, the humic substance is standardized and quantified, using the Dando fulvic acid and the Dando humic acid (as standard samples authorized by the Japanese Humic Substances Society)

Analysis Result

An analysis result obtained according to the above analysis method is presented in Tables 1 to 5. Further, respective three-dimensional excitation-emission matrix fluorescence spectra of the samples and the standard substances are presented in FIGS. 2a to 2h.

TOC of alkali solubles was 44000 mg/L in the case of white birch chips, and 35000 mg/L in the case of willow chips, and TOC after fractionation of fulvic acid was 41000 mg/L in the case of white birch chips, and 34000 mg/L in the case of willow chips. This means that almost the entirety of the obtained solution is the fractionated fulvic acid. Based on the carbon content (47.57%) of the Dando fulvic acid, the TOC values can be converted to concentration values presented in Table 2. However, in observing the three-dimensional fluorescence spectrum, in view of the fact that strong fluorescence peaks are observed around 300 nm in terms of fluorescence wavelength (Em), and 220 nm and 270 nm in terms of excitation wavelength (Ex), actual values are considered to be lower than the converted values.

Converted values from the three-dimensional fluorescence measurement of the fractionated fulvic acid were 7400 mg/L in the case of white birch chips, and 4600 mg/L in the case of willow chips. These values are based on an assumption that a humic substance contained in each of the samples has the same fluorescence property as that of the Dando fulvic acid.

As above, almost the entirety of the obtained solution considered as a fulvic acid solution was a fulvic acid solution.

This evidently proves an advantageous effect of the present invention.

TABLE 1

Result of Measurement of Alkali Solubles

| Analytical Item | Unit | White Birch Chips | Willow Chips |
|---|---|---|---|
| TOC | mg/L | 44000 | 35000 |

TABLE 2

Result of Measurement of TOC in Fractionated Fulvic Acid

| Analytical Item | Unit | White Birch Chips | Willow Chips |
|---|---|---|---|
| TOC | mg/L | 41000 | 34000 |
| Fulvic Acid Converted Concentration (*1) | mg/L | 86000 | 71000 |

(*1) The carbon content of the Dando fulvic acid is 47.57%

TABLE 3

Result of 3-Dimensional Fluorescence Measurement of Fractionated Fulvic Acid

| Analytical Item | Unit | White Birch Chips | Willow Chips |
|---|---|---|---|
| Fluorescence Intensity | — | $2.1 \times 10^{11}$ | $1.3 \times 10^{11}$ |
| QSU Value | QSU | $3.3 \times 10^{8}$ | $2.1 \times 10^{8}$ |
| Fulvic Acid Converted Concentration | mg/L | 7400 | 4600 |

TABLE 4

Result of Measurement of TOC in Fractionated Humic Acid

| Analytical Item | Unit | White Birch Chips | Willow Chips |
|---|---|---|---|
| TOC | mg/L | 960 | 500 |
| Humic Acid Converted Concentration (*2) | mg/L | 1800 | 940 |

(*2) The carbon content of the Dando humic acid is 53.04%

TABLE 4

Result of 3-Dimensional Fluorescence Measurement of Fractionated Humic Acid

| Analytical Item | Unit | White Birch Chips | Willow Chips |
|---|---|---|---|
| Fluorescence Intensity | — | $4.3 \times 10^{9}$ | $3.3 \times 10^{9}$ |
| QSU Value | QSU | $7.0 \times 10^{6}$ | $5.4 \times 10^{6}$ |
| Humic Acid Converted Concentration | mg/L | 190 | 120 |

Further, except that chips of pine and chips of Japanese cedar as needle-leaved trees were used as the raw material, and the processing temperature and pressure were set to higher values than those in the case of broad-leaved trees, an experimental test was performed under the same conditions as those described above. As a result, a larger amount of fulvic acid could be obtained, as compared to the case of broad-leaved trees.

Further, an experimental test of production of a fulvic acid solution was performed by preparing, as the raw material, fragmented pieces of rice straw (Example 3) and fragmented pieces of bamboo (Example 4), and inputting each of the raw materials into the processing space. In each of Examples 3 and 4, the fragmented piece has a long side of about 10 cm on average. In each of Examples 3 and 4, an input amount of the raw material was set to 1.6 m³ (80% of the volume of the processing space). Each of the rice straw and the bamboo was used after drying. Thus, a moderate amount of water was introduced together with the raw material. After input of the raw material, the raw material was subjected to a steam-based subcritical water reaction processing, under stirring by a stirring device, while introducing, into the processing space, steam having a temperature of 180° C. and a pressure of 7 atm in the case of rice straw, or having a temperature of 180° C. and a pressure of 12 atm in the case of bamboo. The processing time was set to 10 minutes when rice straw is used as the raw material, or to 25 minutes when bamboo is used as the raw material.

In a holding period in the processing step, the inside of the processing space during the processing step was kept at a temperature of 180° C. and a pressure of 7 atm in the case of rice straw, or at a temperature of 180° C. and a pressure of 12 atm in the case of bamboo.

After completion of the processing, the processing space was communicated with atmospheric air to set the processing space to atmospheric pressure. Subsequently, only a mixed solution was extracted from the processing apparatus.

This mixed solution was processed in the same manner as that in the case of the woody plant, and then analyzed (analyzed in the same manner as that in Examples 1 and 2).

Analysis Result

TOC of alkali solubles was 30000 mg/L in the case of fragmented pieces of rice straw, and 32000 mg/L in the case of fragmented pieces of bamboo, and TOC after fractionation of fulvic acid was 28000 mg/L in the case of fragmented pieces of rice straw, and 31000 mg/L in the case of fragmented pieces of bamboo. This means that almost the entirety of the obtained solution is the fractionated fulvic acid.

From a result of the three-dimensional fluorescence measurement of the fractionated fulvic acid in each of the solutions, it was ascertained that they are definitely a fulvic acid.

That is, almost the entirety of the obtained solution considered as a fulvic acid solution was a fulvic acid solution.

This evidently proves an advantageous effect of the present invention.

LIST OF REFERENCE SIGNS

10: organic waste processing apparatus
12: hermetic container
14: steam jetting device
16: outlet port
18: separation-collection device
26: opening-closing mechanism 30: stirring device
50: liquid collection unit
52: gravity flow-based collection mechanism
54: liquid collection flow passage
58: liquid inlet
60: opening-closing mechanism
62: pressure equalization device
64: pressure-equalizing communication pipe

The invention claimed is:

1. A fulvic acid solution production method comprising:
an apparatus preparation step of preparing a processing apparatus which comprises: a hermetic container internally having a closeable processing space; a steam jetting device operable to jet high-temperature and high-pressure steam into the hermetic container; a supply section having an opening-closing mechanism and operable to supply a raw material into the hermetic container; a stirring device for stirring the raw material supplied into the hermetic container; and a discharge section having an opening-closing mechanism and operable to discharge, to the outside, a processed liquid produced through processing of the raw material by the steam;
a raw material input step of inputting a raw material containing chips of wood as a primary raw material, from the supply section into the processing space of the hermetic container of the processing apparatus;
a processing step of subjecting the raw material to a subcritical water reaction processing, under stirring, while introducing steam having a temperature of 120 to 250° C. and a pressure of 12 to 35 atm into the processing space in which the raw material is input, to obtain a mixed solution containing fulvic acid, humic acid, and suspended matter of chips of wood and/or fragments thereof; and
a fulvic acid solution taking-out step of separating fulvic acid from the obtained mixed solution to take out a fulvic acid solution.

2. The fulvic acid solution production method as recited in claim 1, wherein the wood is a felled timber or wood scrap.

3. The fulvic acid solution production method as recited in claim 2, wherein the felled timber is obtained from a broad-leaved tree or a needle-leaved tree.

4. The fulvic acid solution production method as recited in claim 3, wherein the broad-leaved tree is at least one selected from the group consisting of white birch (*Betula platyphylla*), willow (*Salicaceae*), chestnut tree (*Castanea crenata*), oak (*Quercus*), and beech (*Fagus crenata*).

5. The fulvic acid solution production method as recited in claim 3, wherein the needle-leaved tree is at least one selected from the group consisting of pine (*Pinus*), Japanese cedar (*Cryptomeria japonica*), Japanese cypress (*Chamaecyparis obtusa*), and Hiba (*Thujopsis dolabrata*).

6. The fulvic acid solution production method as recited in claim 2, wherein the wood scrap is solid wood or plywood.

7. The fulvic acid solution production method as recited in claim 1 wherein the processing step is performed for 1 to 8 hours.

8. The fulvic acid solution production method as recited in claim 3, wherein the primary raw material is a broad-leaved tree, and wherein the pressure of steam to be introduced in the processing step is in the range of 12 to 25 atm.

9. The fulvic acid solution production method as recited in claim 3, wherein the primary raw material is a needle-leaved tree, and wherein the pressure of steam to be introduced in the processing step is in the range of 20 to 35 atm.

10. A fulvic acid solution production method comprising:
an apparatus preparation step of preparing a processing apparatus which comprises: a hermetic container internally having a closeable processing space; a steam jetting device operable to jet high-temperature and high-pressure steam into the hermetic container; a supply section having an opening-closing mechanism and operable to supply a raw material into the hermetic container; a stirring device for stirring the raw material supplied into the hermetic container; and a discharge section having an opening-closing mechanism and operable to discharge, to the outside, a processed liquid produced through processing of the raw material by the steam;
a raw material input step of inputting a plant raw material comprised of a gramineous plant as a primary raw material, from the supply section into the processing space of the hermetic container of the processing apparatus;
a processing step of subjecting the raw material to a subcritical water reaction processing, under stirring, while introducing steam having a temperature of 100 to 200° C. and a pressure of 5 to 25 atm into the processing space in which the raw material is input, to obtain a mixed solution containing fulvic acid and humic acid; and
a fulvic acid solution taking-out step of separating fulvic acid from the obtained mixed solution to take out a fulvic acid solution.

11. The fulvic acid solution production method as recited in claim 10, wherein the plant raw material is felled or mowed plant, or a plant scrap.

12. The fulvic acid solution production method as recited in claim 11, wherein the felled or mowed plant is at least one selected from the group consisting of rice (*Oryza sativa*), wheat (*Triticum aestivum*), barley (*Hordeum vulgare*), oat (*Avena fatua*), rye (*Secale cereale*), proso millet (*Panicum miliaceum*), foxtail millet (*Setaria italica*), Japanese millet (*Echinochloa esculenta*), corn (*Zea mays*), finger millet (*Eleusine coracana*), sorghum (*Sorghum bicolor*), bamboo (*Bambusoideae*), manchurian wild rice (*Zizania latifolia*), sugar cane (*Saccharum officinarum*), adlay (*Coix lacryma-jobi* var. ma-yuen), reed (*Phragmites australis*), Japanese silver grass (*Miscanthus sinensis*), arrow bamboo (*Pseudosasa japonica*), giant reed (*Arundo donax*), pampas grass (*Cortaderia selloana*), and lawn grass.

13. The fulvic acid solution production method as recited in claim 11, wherein the felled or mowed plant is rice straw or wheat straw.

14. The fulvic acid solution production method as recited in claim 12, wherein the felled or mowed plant is bamboo.

15. The fulvic acid solution production method as recited in claim 14, wherein the bamboo is formed in a chip shape.

16. The fulvic acid solution production method as recited in claim 10, wherein the raw material is a post-use plant scrap.

17. The fulvic acid solution production method as recited in claim 16, wherein the plant scrap is an aging tatami mat.

18. The fulvic acid solution production method as recited in claim 10, wherein the processing step is performed for 3 to 30 minutes.

19. The fulvic acid solution production method as recited in claim 1, wherein the raw material is introduced into the processing space in an amount of 90% by volume or less of the processing space.

20. The fulvic acid solution production method as recited in claim 1, wherein the raw material is introduced into the processing space in an amount of 50 to 80% by volume of the processing space.

21. The fulvic acid solution production method as recited in claim 1, wherein the stirring in the processing step is performed by a stirring member rotatably disposed in the processing space.

22. The fulvic acid solution production method as recited in claim 1, wherein the raw material input step includes adding an alkaline solution as an additive.

* * * * *